United States Patent [19]
Kurek et al.

[11] Patent Number: 5,821,326
[45] Date of Patent: Oct. 13, 1998

[54] PROCESS FOR PREPARING MONO AND POLYASPARTATES

[75] Inventors: Gerald Kurek, Leverkusen; Josef Pedain, Köln; Reinhard Halpaap; Michael Sonntag, both of Odenthal, all of Germany

[73] Assignee: Bayer Aktiengesellschaft, Leverkusen, Germany

[21] Appl. No.: 883,478

[22] Filed: Jun. 25, 1997

[30] Foreign Application Priority Data

Jul. 2, 1996 [DE] Germany ................. 196 26 470.7
Apr. 25, 1997 [DE] Germany ................. 197 17 427.2

[51] Int. Cl.$^6$ ............................. C08G 69/26
[52] U.S. Cl. ................. 528/332; 528/335; 528/422
[58] Field of Search ................. 528/332, 422, 528/335

[56] References Cited

U.S. PATENT DOCUMENTS

| | | | |
|---|---|---|---|
| 5,126,170 | 6/1992 | Zwiener et al. | 427/385.5 |
| 5,214,086 | 5/1993 | Mormile et al. | 524/237 |
| 5,236,741 | 8/1993 | Zwiener et al. | 427/385.5 |
| 5,243,012 | 9/1993 | Wicks et al. | 528/58 |
| 5,364,955 | 11/1994 | Zwiener et al. | 556/418 |
| 5,412,056 | 5/1995 | Zwiener et al. | 528/73 |
| 5,489,704 | 2/1996 | Squiller et al. | 560/35 |
| 5,623,045 | 4/1997 | Zwiener et al. | 528/68 |

FOREIGN PATENT DOCUMENTS 667362   8/1995   European Pat. Off. .

OTHER PUBLICATIONS

Organikum, p. 502, 16 edition, VEB Deutscher Verlag der Wissenschaft, Berlin (month unavailable) 1986.

*Primary Examiner*—Terressa Mosley
*Attorney, Agent, or Firm*—Joseph C. Gil; Thomas W. Roy

[57] ABSTRACT

The present invention relates to a new process for preparing mono and polyaspartates from primary mono and polyamines and maleates in presence of five-membered aromatic ring compounds containing nitrogen atoms in the ring structure as catalysts and use of these mono and polyaspartates as reactive components for polyisocyanates in two-component polyurethane coating compositions and for preparing polyurethane prepolymers.

15 Claims, No Drawings

PROCESS FOR PREPARING MONO AND POLYASPARTATES

BACKGROUND OF THE INVENTION

1. Field of the Invention

The present invention relates to a new process for preparing aspartates from primary amines and maleates in the presence of certain aromatic ring compounds and to their use as reactive components for polyisocyanates in two-component polyurethane coating compositions and for preparing polyurethane prepolymers.

2. Description of the Prior Art

Two-component coating compositions which contain, as binder, a polyisocyanate component combined with an isocyanate-reactive component, in particular a polyhydroxyl compound, are known. They are suitable for preparing high quality coatings which are hard, elastic, abrasion resistant, solvent resistant and weather resistant.

Recently, specific secondary polyamines which contain ester groups have become firmly established in the two-component surface coating industry. They are particularly suitable, in combination with lacquer polyisocyanates, as binders in low-solvent or solvent-free, high solids coating compositions because they provide rapid curing of the coatings at low temperatures.

These secondary polyamines are polyaspartates, such as those described in EP-A-0,403,921. Their use as the only isocyanate-reactive component or mixed with other isocyanate-reactive components in two-component coating compositions is described in EP-A 0,403,921, 0,639,628, 0,667,362, 0,689,881, U.S. Pat. No. 5,214,086, EP-A 0,699, 696, 0,596,360 and U.S. Pat. No. 5,243,012.

A suitable process for preparing these polyaspartates is the reaction of the corresponding primary polyamines with maleates or fumarates corresponding to the formula $$R^1OOC-CH=CH-COOR^2$$

wherein $R^1$ and $R^2$ are identical or different organic groups, resulting in the formation of secondary polyamines. Due to stearic, structural and electronic effects, these secondary amino groups have sufficiently reduced reactivity towards isocyanate groups to be mixed with polyisocyanates in a reliable and easy manner.

The reaction which is used to prepare polyaspartates is the addition of primary amines to the activated C—C double bond in vinyl carbonyl compounds, which has been described in the literature (see Chem. Ber. 1946, 38, 83; Houben Weyl, Meth. d. Org. Chemie, vol. 11/1, 272 (1957); Usp. Chimii 1969, 38, 1933). It has been found, however, that this reaction does not proceed to completion during the course of the actual synthesis process (e.g., 24 hours with stirring at 60° C.). The actual extent of the reaction is dependent upon the type of primary polyamine. Thus, the degree of conversion (measured by the concentration of free, unconverted maleate and fumarate, into which maleate rearranges in the presence of basic catalysts) after 1 day with 1,6-hexanediamine is about 90 to 93%. The degree of conversion after 1 day with a cycloaliphatic polyamine having sterically hindered primary amino groups, i.e., 4,4'-diamino-3,3'-dimethyldicyclohexyl-methane (Laromin C260, BASF), is only 77%. Complete or essentially complete conversion is achieved only after several days or, in the case of 4,4'-diamino-3,3'-dimethyldicyclohexyl-methane, only after several months.

Before complete conversion is obtained, these products contain unreacted primary amino groups and even free primary polyamines as well as the equivalent amount of unreacted maleate or fumarate. This causes handling difficulties during the processing procedure due to the vigorous reaction of primary amino groups with isocyanate groups and to poorer properties in the resulting coating, such as reduced scratch resistance, which substantially restricts the use of these products. These products also have a disadvantage from a toxicological point of view.

Extending the reaction time or increasing the reaction temperature to 80° C., or even 100° C., to accelerate the reaction is not a satisfactory solution because this drastically increases the color index of the product.

Extending the pot life of two-component binders based on polyisocyanates and polyaspartates by adding zeolites or organotin(IV) compounds is described in EP-A 0,667,362 and U.S. Pat. No. 5,243,012. However, these measures were not intended to overcome the problems associated with incomplete conversion.

It is an object of the present invention to accelerate the aspartate synthesis reaction by adding one or more catalysts such that after an economically acceptable synthesis time, mono and polyaspartates are obtained, which satisfy the requirements for color, ease-of-use and reactivity, without having to store the product for any particular time.

Surprisingly, this object may be achieved by adding certain catalysts according to the present invention. Although catalysis of additions to vinyl double bonds is known (Organikum, p.502, 16th edition, VEB Deutscher Verlag der Wissenschaft, Berlin 1986), it has been shown that most of the catalysts that have been disclosed not only accelerate the reaction, they also lead to a drastic, unacceptable darkening of the color of the product.

Accordingly, the catalysts must possess the following properties:

a) they must greatly accelerate the reaction for preparing polyaspartates, b) they must not promote secondary reactions which could under the proper circumstances lead to discoloration of the product, c) they should suppress discoloration of the reaction mixture both during and also after the synthesis process, in particular during the mixing procedure with other compounds which are reactive towards isocyanate groups, d) they should exert no effect on the reaction of polyaspartates and optionally other isocyanate-reactive components with polyisocyanates and e) they should not impair the properties of the final coating.

It has been found that five-membered aromatic ring compounds containing two, three or four nitrogen atoms in the ring structure are suitable catalysts for the preparation of mono and polyaspartates from primary mono and polyamines and maleates or fumarates and satisfy conditions a) to e) mentioned above.

SUMMARY OF THE INVENTION

The present invention relates to a process for preparing secondary mono and polyamines corresponding to formula (I),

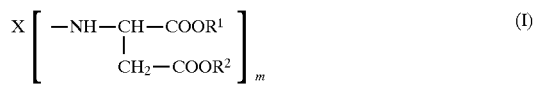

by reacting at a temperature of 0° to 100° C., in solution or in the absence of a solvent and at an equivalent ratio of primary amino groups in component A to C=C double bonds in component B of 1:2 to 1.5:1

A) mono or polyamines corresponding to formula (II)

$$X[-NH_2]_m \quad (II)$$

with

B) compounds corresponding to formula (III)

$$R^1OOC-CH=CH-COOR^2 \quad (III)$$

in the presence of 0.1 to 10 wt. %, preferably 0.1 to 5 wt. % and more preferably 0.1 to 2 wt. %, based on solids, of a catalyst component C corresponding to formulas (IV) to (XI)

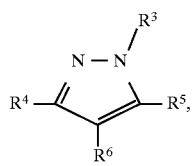 (IV)

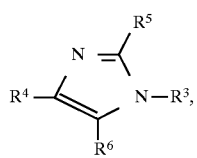 (V)

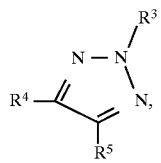 (VI)

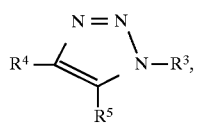 (VII)

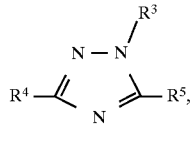 (VIII)

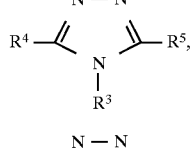 (IX)

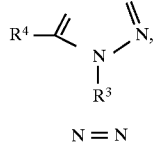 (X)

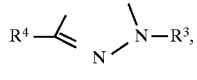 (XI)

and optionally distilling off excess reactants at the end of reaction,
wherein

X represents an m-valent organic residue obtained by removing the primary amino group or groups from a mono or polyamine which has (cyclo)aliphatically bound amino groups and a number average molecular weight of 60 to 6000, and which may contain further functional groups that either are reactive with isocyanate groups or are inert to isocyanate groups at temperatures of up to 100° C., $R^1$ and $R^2$ are the same or different and represent an organic group, $R^3$ represents an $NH_2$ group, a hydrogen atom or an organic group having 1 to 24 carbon atoms, $R^4$, $R^5$ and $R^6$ are the same or different and represent an $NH_2$ group, a hydrogen atom or an organic group having 1 to 24 carbon atoms, or one or more of these groups may optionally be a constituent of another ring system, and m represents an integer $\geq 1$.

The present invention also relates to a two-component coating composition which contains, as binder, a) a polyisocyanate component and
b) an isocyanate-reactive component containing
   b1) a compound corresponding to formula (I) and prepared by the process according to the invention and
   b2) optionally other isocyanate-reactive compounds, wherein the equivalent ratio of isocyanate groups to isocyanate-reactive groups is 0.8:1 to 20:1, and optionally additives well known in surface coatings technology.

Finally, the present invention also relates to prepolymers containing urea, urethane, allophanate and/or biuret structures, which are based on the reaction product of polyisocyanates with the mono and polyaspartates prepared according to the invention, optionally in admixture with one or more isocyanate-reactive components.

DETAILED DESCRIPTION OF THE INVENTION

In the preceding formulas X preferably represents an m-valent organic residue obtained by removing the primary amino group or groups from a mono or polyamine which has (cyclo)aliphatically bound amino groups and a number average molecular weight of 88 to 322, and which may contain further functional groups that either are reactive with isocyanate groups or are inert to isocyanate groups at temperatures of up to 100° C. In addition, $R^1$ and $R^2$ are the same or different and represent organic groups, preferably alkyl groups, having 1 to 18 carbon atoms, preferably 1 to 8 carbon atoms. Also, in accordance with the present invention, organic groups X and $R^1$ to $R^6$ may contain heteroatoms, such as N, O, S or Si, and m preferably represents an integer $\geq 2$, more preferably 2.

Any known mono and polyamines having at least one primary amino group may be used as component A. Suitable primary monoamines (m=1) include monoamines wherein organic group X contains one or more other functional groups that are either reactive with isocyanate groups or inert to isocyanate groups. The isocyanate-reactive groups, such as hydroxyl, secondary amino and carboxyl groups, represent additional reaction partners for isocyanate groups. The inert functional groups may provide alternative cross-linking mechanisms, such as moisture curing, or improved compatibility with other additives (solvents, pigments, etc.) or better adhesion of the coatings to certain substrates.

Examples of primary monoamines include aminoalcohols such as ethanolamine; and aminoalkylalkoxysilanes and aminoalkylalkylsilanes corresponding to the formula $$H_2N-R^7-SiR^8R^9R^{10}$$

wherein $R^7$ is an alkylene group with 2 to 6 carbon atoms and $R^8$, $R^9$ and $R^{10}$ are the same or different and represent chlorine atoms or alkyl and/or alkoxy groups having 1 to 4 carbon atoms.

Suitable polyamines (m $\geq$ 2) include ethylenediamine, 1,2-diaminopropane, 1,4-diaminobutane, 2,5-diamino-2,5- dimethylhexane, 1,5-diamino-2-methyl-pentane (Dytec A, DuPont), 1,6-diaminohexane (HDA), 2,2,4- and/or 2,4,4-trimethyl-1,6-diaminohexane, 1,11-diaminoundecane, 1,12-diamino-dodecane, 1-amino-3,3,5-trimethyl-5-aminomethylcyclohexane (IPDA), 2,4- and/or 2,6-hexahydrotoluylene-diamine ($H_6$TDA), isopropyl-2,4- and/or 2,6-diamino-cyclohexane, 2,4'- and/or 4,4'-diaminodicyclohexylmethane (HMDI), 3,3'-dimethyl-4,4'-diaminodicyclohexylmethane (Laromin C 260, BASF), the isomers of diaminodicyclohexylmethane having a methyl group as a ring-substituent, 3(4)-aminomethyl-1-methylcyclohexylamine (AMCA), and polyether-polyamines having aliphatically bound primary amino groups, such as Jeffamine resins available from Huntsman.

Component B, which corresponds to formula (III), comprises maleates and fumarates. Suitable maleates or fumarates for preparing mono or polyaspartates in accordance with the invention include dimethyl, diethyl, di-n-propyl, di-isopropyl, di-n-butyl and di-2-ethylhexyl maleates or the corresponding fumarates.

Catalyst component C is selected from the five-membered aromatic ring compounds containing heteroatoms corresponding to formulas (IV) to (XI). These include the pyrazoles corresponding to formula (IV) and imidazoles corresponding to formula (V), which contain 2 nitrogens; the 1,2,3-triazoles corresponding to formulas (VI) and (VII) and 1,2,4-triazoles corresponding to formula (VIII) and (IX), which contain 3 nitrogens; the tetrazoles corresponding to formulas (X) and (XI), which contain 4 nitrogen atoms.

$R^3$, which is bound to a ring nitrogen atom in formulas (IV) to (XI), represents an $NH_2$ group, a hydrogen atom or an organic group having 1 to 24 carbon atoms, preferably a hydrogen atom. $R^4$, $R^5$ and $R^6$, which are bound to ring carbon atoms in formulas (IV) to (XI), are the same or different and represent an $NH_2$ group, a hydrogen atom, an organic group having 1 to 24 carbon atoms, or one or more of these groups may optionally be a constituent of another ring system.

Compounds which are particularly preferred as component C are those corresponding to formula (IV) to (XI) in which $R^3$ represents a hydrogen atom and $R^4$, $R^5$ and $R^6$ are the same or different and represent an $NH_2$ group, a hydrogen atom or an organic group having 1 to 6 carbon atoms. Examples of these compounds include 1,2,4-triazole, 3,5-dimethyl-1,2,4-triazole, 3,5-dimethylpyrazole and 1H-imidazole.

Mono and polyaspartates corresponding to formula (I) are prepared by reacting component A with component B in the presence of component C at temperatures of 0° and 100° C., preferably 20° to 80° C. and more preferably 20° to 60° C. wherein (i) the equivalent ratio of primary amino groups in component A to C=C double bond equivalents in component B is 1:2 to 1.5:1, preferably 1:1.2 to 1.2:1 and (ii) catalyst component C is present in an amount of 0.1 to 10 wt. %, preferably 0.1 to 5 wt. % and more preferably 0.1 to 2 wt. %, based on solids. The reaction time may be 8 hours to 4 days, depending upon the type of mono or polyamine and the desired maximum residual concentration of reactants in the reaction mixture. Excess reactants can be distilled off at the end of reaction.

In accordance with one embodiment of the present invention the amine component (component A) is initially introduced together with 1 wt. % (based on the solids content components A, component B and component C) of catalyst component C. This mixture is heated to 60° C. and component B is added at this temperature over the course of 8 h, with stirring, such that the ratio of primary amino groups in component A to C=C double bonds in component B is 1:1. After the dropwise addition, stirring is continued for another 3½ to 4 days at 60° C. and then the mixture is cooled.

Components A, B and C are selected from the individual compounds from each of the relevant groups of compounds or a mixture of two or more compounds from each of the relevant groups of compounds.

The process according to the invention of the mono or polyaspartates may be either be performed in solution or in the absence of a solvent. Solvent may also be added after the synthesis process, for example, to lower the viscosity. Suitable solvents include any organic solvents, preferably those known from surface coating technology. Examples include acetone, methyl ethyl ketone, methyl isobutyl ketone, n-butyl acetate, methoxypropyl acetate, toluene, xylene and higher aromatic solvents (such as the Solvesso solvents form Exxon).

Following synthesis of the mono and polyaspartates, catalyst component C and, thus, the synthesis process according to the invention can still be detected by gas chromatographic methods.

The mono and polyaspartates prepared according to the invention may be directly used as reactive components for polyisocyanates after concluding the synthesis process due to the almost complete degree of conversion.

One use according to the invention for the mono and poly-aspartates prepared according to the invention is to prepare coatings from two-component coating compositions containing, as binder, a) a polyisocyanate component and
b) an isocyanate-reactive component containing
b1) mono or polyaspartates corresponding to formula (I) and
b2) optionally other known isocyanate-reactive components, Suitable polyisocyanate components a) are known and include the polyisocyanates known from polyurethane chemistry, e.g, low molecular weight polyisocyanates and lacquer polyisocyanates prepared from these low molecular weight polyisocyanates. Preferred are the lacquer polyisocyanates, which are known from surface coating technology. These lacquer polyisocyanates contain biuret groups, isocyanurate groups, allophanate groups, uretdione groups, carbodiimide groups and/or urethane groups and are preferably prepared from (cyclo)aliphatic polyisocyanates.

Suitable low molecular weight polyisocyanates for use in accordance with the present invention or for preparing the lacquer polyisocyanates are those having a molecular weight of 140 to 300, such as 1,4- tetramethylene diisocyanate, 1,6-hexamethylene diisocyanate (HDI), 2,2,4- and/or 2,4,4-trimethyl-hexamethylene diisocyanate, dodecamethylene diisocyanate, 2-methyl-1,5-diisocyanatopentane, 1,4-diisocyanatocyclohexane, 1-isocyanato-3,3,5-trimethyl-5-isocyanato-methyl-cyclohexane (IPDI), 2,4- and/or 4,4' diisocyanato-dicyclohexyl-methane, 1-isocyanato-1-methyl-3(4)-isocyanatomethyl-cyclohexane (IMCI), 2,4- and/or 2,6-hexahydrotoluylene diisocyanate ($H_6$TDI), 2,4- and/or 4,4'-diisocyanatodiphenyl-methane or mixtures of these isomers with their higher homologs (which may be obtained in known manner by the phosgenation of aniline/formaldehyde condensates), 2,4- and/or 2,6-diisocyanatotoluene, and mixtures thereof. The use of low molecular weight polyisocyanates themselves is not preferred. Also lacquer polyisocyanates prepared from aromatic polyisocyanates, such as 2,4- and/or 2,6-diisocyanatotoluene, are also less preferred. The lacquer polyisocyanates containing urethane groups are preferably based on low molecular weight polyhydroxyl compounds having molecular weights of 62 to 300, such as ethylene glycol, propylene glycol and/or trimethylol-propane.

Preferred lacquer polyisocyanates for use as component a) are those based on 1,6-hexamethylene diisocyanate and having an NCO content of 16 to 24 wt. % and a maximum viscosity at 23° C. of 10,000, preferably 3000 mPa.s.

Component b1) is selected from mono and polyaspartates corresponding to formula (I), preferably those in which m is 2. Preferably, X represents a divalent hydrocarbon group obtained by removing the amino groups from, 1-amino-3,3,5-trimethyl-5-aminomethyl-cyclohexane (IPDA), 4,4'-diaminocyclohexylmethane (HMDI), 3,3'- dimethyl-4,4'-diaminodicyclohexylmethane (Lasomin C260, BASF), hexahydro-2,4- and/or 2,6-diaminotoluene (H$_6$TDA), isomers of C-monomethyl-diaminodicyclohexyl-methanes or 3(4)-aminomethyl-1-methylcyclohexylamine (AMCA).

Preferred starting components b1) include those compounds corresponding to formula (I) in which $R^1$ and $R^2$ represent methyl, ethyl, n-propyl, isopropyl, n-butyl or 2-ethylhexyl groups.

Optional starting components b2) are known compounds containing at least two isocyanate-reactive groups, including groups which react with isocyanate groups under the effect of either moisture or/and heat. Examples include the hydroxy-functional polyacrylates and polyesterpolyols described in EP-A 0,689,881 (Canadian Application No. 2,148,318), the oxazolidines described in EP-A 0,639,628 (Canadian Application No. 2,130,166) and the polyaldimines and polyketimines described in EP-A 0,699,696 (U.S. Pat. No. 5,489,704, herein incorporated by reference). Mixtures of these compounds may also be used.

In the binders used according to the invention, the amounts of components a), b1) and (optionally) b2) are selected such that the equivalent ratio isocyanate groups to isocyanate-reactive groups is 0.8:1 to 20:1, preferably 0.8:1 to 1.2:1. When calculating this ratio, the oxazolidine rings in monocyclic mono or polyoxazolidines are considered to be difunctional groups in the isocyanate addition reaction.

The binders according to the invention are prepared by mixing the individual components either in the absence of a solvent or in the presence of the solvents which are conventionally used in polyurethane surface coating technology. Suitable solvents include ethyl acetate, butyl acetate, methoxypropyl acetate, methyl isobutyl ketone, methyl ethyl ketone, xylene, N-methylpyrrolidone, petroleum spirit, chlorobenzene, Solvesso solvent or mixtures thereof.

Preferably, the ratio by weight binder components a) and b) to solvent in the coating compositions according to the invention is 40:60 to 100:0, more preferably 60:40 to 90:10.

The coating compositions may also contain the known additives from surface coating technology. These include pigments, fillers, flow control agents, catalysts and anti-settling agents.

The properties of the coatings obtained from the coating compositions according to the invention may be adjusted by appropriate selection of the type and ratios of starting components a), b1) and b2).

The coating compositions may be applied to any substrate in a single layer or in several layers by known methods, e.g., by spraying, painting, immersing, flooding or by using rollers or spreaders. The coating compositions according to the invention are suitable for preparing coatings on substrates, such as metals, plastics, wood or glass. The coating compositions are especially suitable for coating steel sheeting, which is used for the production of vehicle bodies, machines, cladding panels, barrels and containers. The substrates may be provided with suitable primer coats prior to applying the coating compositions according to the invention. Drying of the coatings may take place at a temperature of about 0° to 160° C.

The process for producing coatings using the mono and poly-aspartates prepared according to the invention may also be used for the production of prepolymers containing urea, urethane, allophanate and/or biuret structures. To prepare these prepolymers, the mono and poly-aspartates, which are used as component b1), are preferably selected from compounds in which the organic group X includes one or more other functional groups which are inert towards isocyanate groups at temperatures of up to 100° C. These functional groups offer the possibility of alternative cross-linking mechanisms such as moisture hardening.

Examples of these compounds include the monoaspartates corresponding to formula (XII), which contain alkoxysilane, alkylsilane and/or alkoxyalkylsilane groups:

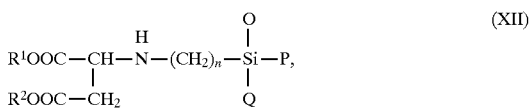

wherein
$R^1$ and $R^2$ are as previously defined,
n is an integer $\geq 2$ and
O, P and Q are the same of different and represent $C_1$–$C_4$-alkyl and/or $C_1$–$C_{14}$-alkoxy groups.

The mono and polyaspartates prepared according to the invention may be directly used after completion of the synthesis process because, in contrast to prior art mono and polyaspartates prepared without catalysis, an approximately complete degree of conversion is achieved. As a result of the low concentration of maleates, fumarates and primary amino groups, these products are not only toxicologically and physiologically harmless, they also exhibit a reasonable, as opposed to a vigorous, reactivity towards isocyanates. Due to their low viscosity, they are a more than suitable alternative, as reactive diluents, to the environmentally polluting organic solvents previously used and may therefore be used in high quality, low-solvent or even solvent-free high solids two-component coating compositions.

The following examples demonstrate the catalytic effect of five-membered aromatic ring systems containing one or more nitrogen atoms in the ring structure in the synthesis of mono and polyaspartates by the addition of primary mono and polyamines to maleates or fumarates.

Reactions are described with and, for comparison, without the addition of catalysts according to the invention. The particular percent conversion directly after conclusion of the preparation process, the properties of the polyaspartates (viscosity, color) and their reactivity with polyisocyanates (gel time, film formation and film properties) are set forth.

All parts and percentages are by weight, unless otherwise indicated.

EXAMPLES

A) Analytical Chemistry Relating to Polyaspartates

Determination of the concentration of unreacted fumarate (into which maleate rearranges in the presence of basic catalysts) was performed by Supercritical Fluid Chromatography (SFC) using a SFC 3000 instrument from the Carlo Erba Co.

The values are given as amounts in weight percentages. The degree of conversion is calculated from this data, based on a 1:1 equivalent ratio of primary amino groups to C=C double bonds in the maleate or fumarate, using the following formula:

Degree of conversion [%] =
$$100 - \frac{[F] \cdot (n_A \cdot \text{Equiv}_A + n_A \cdot \text{Equiv}_F + M_c)}{n_A \cdot \text{Equiv}_F}$$

$n_A$: number of equivalents of primary amino groups or equivalents of double bonds (fumarate)
$\text{Equiv}_A$: equivalent weight of the polyamine, based on $NH_2$ groups, in g
[F]: concentration of unreacted fumarate (F) in wt. %
$\text{Equiv}_F$: equivalent weight of fumarate, based on C=C bonds (1 Equiv=1 mole), in g
$M_C$: amount of catalyst component C used in g (=0 if no catalyst)
Since primary diamines ($n_A$=2) and diethyl fumarate (DEF, $M_{DEF}$=172.18 g) were exclusively used in the following examples, the preceding equation simplifies to $$\text{Degree of conversion [\%]} = 100 - \frac{[DEF] \cdot (2 \cdot \text{Equiv}_A + 344.36 \text{ g} + M_c)}{344.36 \text{ g}}$$

The viscosities were determined at 23° C. using a rotary viscosimeter "Viscotester VT 181" from the Haake Co.

The catalysts according to the invention, i.e., 1,2,4-triazole, 3,5-dimethyl-1,2,4-triazole and 3,5-dimethylpyrazole, were prepared using common laboratory methods.

B) Preparation of Polyaspartates
I) General Procedure for Preparing Polyaspartates Without Catalysts (Comparison Examples)

2 equivalents of a diamine (1 mole) were initially introduced into a 1 liter four-necked flask with a stirrer, dropping funnel, reflux condenser and internal thermometer, under an atmosphere of nitrogen and heated to 60° C. and then 2 equivalents of diethyl maleate (344.36 g, 2 moles) were added at this temperature over a period of 8 hours with stirring. Stirring was continued at 60° C. for 3 to 4 days. A gentle stream of nitrogen was passed over the reaction mixture throughout the entire reaction time.

II) General Procedure for Preparing Polyaspartates According to the Invention by Catalysis With 3,5-dimethylpyrazole and 1,2,4-triazoles.

The procedure as described under I) was followed with the exception that 1 wt. %, based on the solids content of the reaction batch, of was initially introduced with the diamine.

Example 1
Comparison Example for Examples 2, 3 and 4
238.4 g 3,3'-dimethyl-4,4'-diamino-dicyclohexylmethane (Laromin C 260, BASF; 2 equivalents)
344.4 g diethyl maleate (DEM; 2 equivalents)
Reaction temperature 60° C.
Reaction time
a) 1 day
b) 2 days
c) 4 days a) After 1 day the reaction mixture had a viscosity of 330 mPa.s/23° C. The concentration of DEF was 14%, which corresponded to a percent conversion of 76.3%. After 8 months storage at room temperature, a degree of conversion of 94.4% (=3.3% DEF) was achieved. There was a drastic increase in viscosity to 2100 mPa.s/23° C. during this time and the previously pale yellow product had acquired an intense yellow color.
b) After 2 days the DEF concentration (in-situ measurement) was 9.5% which corresponded to a percent conversion of 87.1%.
c) After 4 days the DEF concentration was 4.8%, which corresponded to a percent conversion of 93.5%. The product had a viscosity of 1110 mPa.s/23° C. and an intense yellow color.

In examples 2, 3 and 4, described below, a higher percent conversion immediately after the end of the synthesis process was achieved by the addition of 1 wt. % of catalyst. The viscosity values are another indication of the completeness of reaction.

Example 2

According to the Invention, Comparison for Example 1

238.4 g 3,3-dimethyl-4,4'-diamino-dicyclohexylmethane (2 equiv.)

344.4 g diethyl maleate (2 equiv.)

5.9 g 1,2,4-triazole as catalyst (MW=69.07 g)

Reaction time: 1 day

DEF conc.: 7.6%

Percent conversion: 87.0%

Viscosity [mPa.s/23° C.] 750

Color: pale yellow

Example 3

According to the Invention, Comparison for Example 1

238.4 g  3,3-dimethyl-4,4'-diamino-dicyclohexylmethane (2 equiv.)
344.4 g  diethyl maleate (2 equiv.)
5.9 g    3,5-dimethyl-1,2,4-triazole (MW = 97.12 g)

| Reaction time | a) 1 day | b) 2 days | c) 4 days |
|---|---|---|---|
| DEF conc. | 9.2% | 6.0% | 3.3% |
| Percent conversion | 84.3% | 89.7% | 94.4% |
| Viscosity [mPa · s/23° C. | 630 | — | 1650 |
| color | colorless | colorless | pale yellow |

Example 4

According to the Invention, Comparison for Example 1

238.4 g  3,3-dimethyl-4,4'-diamino-dicyclohexylmethane (2 equiv.)
344.4 g  diethyl maleate (2 equiv.)
5.9 g    3,5-dimethylpyrazole as catalyst (MW = 96.13 g)

| Reaction time | a) 1 day | b) 2 days | c) 4 days |
|---|---|---|---|
| DEF conc. | 8.1% | 5.8% | 3.8% |
| Percent conversion | 86.2% | 90.1% | 93.5% |
| Viscosity [mPa · s/23° C.] | 630 | — | 1380 |
| Color | colorless | colorless | pale yellow |

It is apparent from examples 3 and 4 that when using 3,3-dimethyl-4,4'-diamino-dicyclohexylmethane as the diamine component, a reaction time of 4 days at 60° C. and use of catalysts according to the invention was sufficient to obtain an almost fully matured product. To the contrary the conventional method, 1 day at 60° C. (comparison example 1) followed by storage at room temperature, provided a product with a corresponding percent conversion only after 4 to 8 months storage time.

Example 5

Comparison Example for Examples 6 and 7

| 210.4 g | 4,4'-diaminodicyclohexylmethane (HMDI; 2 equiv.) |
| 344.4 g | diethyl maleate (2 equiv.) |

| Reaction time | a) 1 day | b) 2 days | c) 4 days |
| --- | --- | --- | --- |
| DEF concentration | 7.26% | 4.7% | 2.67% |
| Percent conversion | 88.2% | 92.3% | 95.7% |
| Viscosity [mPa · s/23° C.] | 600 | — | 1350 |
| Color | colorless | pale yellow | pale yellow | a) If the reaction was terminated after 1 day and the product was then stored at room temperature, it took 16 weeks to achieve a percent conversion of 97.9%.

Example 6

According to the Invention, Comparison for Example 5

| 210.4 g | 4,4'-diaminodicyclohexylmethane (2 equiv.) |
| 344.4 g | diethyl maleate (2 equiv.) |
| 5.6 g | 3,5-dimethyl-1,2,4-triazole as catalyst |

| Reaction time | a) 1 day | b) 2 days | c) 4 days |
| --- | --- | --- | --- |
| DEF conc. | 5.6% | 3.5% | 2.8% |
| Percent conversion | 90.9% | 94.3% | 95.4% |
| Viscosity [mPa · s/23° C.] | — | — | 1800 |
| Color | colorless | colorless | pale yellow |

Example 7

According to the Invention, Comparison for Example 5

| 210.4 g | 4,4'-diaminodicyclohexylmethane (2 equiv.) |
| 344.4 g | diethyl maleate (2 equiv.) |
| 5.6 g | 3,5-dimethylpyrazole as catalyst |

| Reaction time | a) 1 day | b) 2 days | c) 4 days |
| --- | --- | --- | --- |
| DEF conc. | 3.6% | 2.0% | 1.3% |
| Percent conversion | 94.1% | 96.8% | 97.9% |
| Viscosity [mPa · s/23° C.] | — | — | 1740 |
| Color | colorless | colorless | pale yellow |

Example 8

Comparison Example for Examples 9 and 10

| 128.2 g | 2,4- and 2,6-hexahydrotoluylenediamine (H$_6$TDA, 80:20 mixture of 2,4 and 2,6 isomers; 2 equiv.) |
| 344.4 g | diethyl maleate (2 equiv.) |

| Reaction time | a) 1 day | b) 2 days | c) 4 days |
| --- | --- | --- | --- |
| DEF conc. | 13.9% | 9.6% | 6.3% |
| Percent conversion | 80.7% | 86.7% | 91.3% |
| Viscosity [mPa · s/23° C.] | 180 | — | 195 |
| Color | yellow | deep yellow | deep yellow |

Example 9

According to the Invention, Comparison for Example 8

| 128.2 g | 2,4- and 2,6-hexahydrotoluylenediamine (2 equiv.) |
| 344.4 g | diethyl maleate (2 equiv.) |
| 4.8 g | 3,5-dimethyl-1,2,4-triazole as catalyst |

| Reaction time | a) 1 day | b) 2 days | c) 4 days |
| --- | --- | --- | --- |
| DEF conc. | 9.6% | 6.4% | 4.4% |
| Percent conversion | 86.7% | 91.1% | 93.9% |
| Viscosity [mPa · s/23° C.] | — | — | 300 |
| Color | yellow | yellow | deep yellow |

Example 10

According to the Invention, Comparison for Example 8

| 128.2 g | 2,4- and 2,6-hexahydrotoluylenediamine (2 equiv.) |
| 344.4 g | diethyl maleate (2 equiv.) |
| 4.8 g | 3,5-dimethylpyrazole as catalyst |

| Reaction time | a) 1 day | b) 2 days | c) 4 days |
| --- | --- | --- | --- |
| DEF conc. | 8.9% | 6.1% | 4.3% |
| Percent conversion | 87.7% | 91.5% | 94.0% |
| Viscosity [mPa · s/23°C.) | — | — | 270 |
| Color | yellow | yellow | deep yellow |

Example 11

Comparison Example for Examples 2, 3 and 4

| 238.4 g | 3,3'-dimethyl-4,4'-diamino-dicyclohexylmethane (2 equiv.) |
| 344.4 g | diethyl maleate (2 equiv.) |
| 5.9 g | 1,5-diazabicyclo[4.3.0]non-5-ene |

After a reaction time of 1 day at 60° C., a DEF concentration of 7.9% was found in the reaction mixture, which corresponded to a percent conversion of 86.5% (viscosity 540 mPa.s/23° C.). However, this product, in contrast to the products of examples 2a, 3a and 4a, which were pale yellow or colorless, had a deep yellow-orange color.

C) Coating Compositions

In the following examples coating compositions combinations containing polyaspartates prepared in the examples 1–10 and a polyisocyanate component were prepared.

To determine the gel times and to produce coatings, mixtures of the individual polyaspartates set forth in the following table with an isocyanurate-containing polyisocyanate prepared from 1,6-hexamethylene diisocyanate (Desmodur N 3300 from Bayer AG, viscosity: 3000 ./23° C., NCO content: 21.6%, equivalent weight: 195 g) were prepared at an 1:1 equivalent ratio of NCO groups to NCO-reactive groups and mixed with butyl acetate to obtain a solids content of 80%.

In the following examples the gel time was the time interval from mixing the components to the time when the mixture could not be stirred.

Films were applied to previously degreased glass sheets with a spreader blade and dried at room temperature. The thickness of the layer was 90 μm in all cases; drying was performed at room temperature.

The solvent resistance of the coatings was determined by placing a wad of cotton wool soaked with solvent on the surface of the lacquer for one minute (0=film unchanged, 5=film broken down).

The test for pencil hardness of the coatings was determined by scratch tests with lead pencils of different hardness. The minimum hardness which was required to produce a scratch in the surface of the film is set forth (HB=very soft, H=soft, 3H=very hard).

Equivalent weights of polyaspartates based on diethyl maleate and
(i) 3,3'-dimethyl-4,4'-diaminodicyclohexylmethane (examples 1–4, 11): about 292 g/NH
(ii) 4,4'-diaminodicyclohexylmethane (examples 5 to 7): about 278 g/NH
(iii) 2,4 and 2,6-hexahydrotoluylenediamine (examples 8 to 10): about 237 g/NH In the case of polyaspartates prepared according to the invention, these values must be corrected by a factor of $$\frac{1}{0\cdot 99}$$ (1 wt. % of catalyst added).

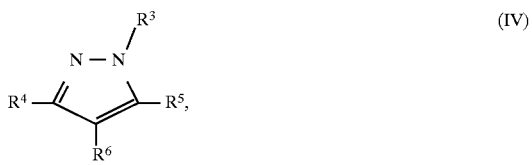

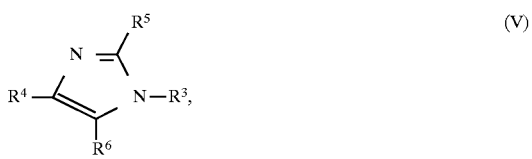

TABLE 1

| | Coating compositions containing polyisocyanates and polyaspartates | | | | | | | | | | | |
|---|---|---|---|---|---|---|---|---|---|---|---|---|
| Example No. | 12 Comp | 13 Comp | 14 Comp | 15 | 16 | 17 | 18 Comp | 19 | 29 | 21 Comp | 22 | 23 |
| Polyaspartate from example no. | 1a | 1a* | 1c | 2 | 3c | 4c | 5c | 6c | 7c | 8c | 9c | 10c |
| Amount [g] | 292 | 292 | 292 | 295 | 295 | 295 | 278 | 281 | 281 | 237 | 240 | 240 |
| contains catalyst[1] | — | — | — | 1,2,4-triazole | DMT | DMP | — | DMT | DMP | — | DMT | DMP |
| Desmodur N 3300 [g] | 195 | 195 | 195 | 195 | 195 | 195 | 195 | 195 | 195 | 195 | 195 | 195 |
| Butyl acetate [g] | 122 | 122 | 122 | 123 | 123 | 123 | 118 | 119 | 119 | 108 | 109 | 109 |
| Gelling time [h] | 21 | >24 | <24 | >24 | >24 | >24 | 3 | 3.5 | 3.5 | >8 | >8 | >8 |
| Solvent resistance | | | | | | | | | | | | |
| Methoxypropyl acetate | 2 | 0 | 2 | 1 | 0 | 0 | 0 | 0 | 0 | 1 | 2 | 2 |
| Xylene | 2 | 0 | 0 | 0 | 0 | 0 | 0 | 0 | 0 | 1 | 1 | 1 |
| Ethyl acetate | 2 | 0 | 1 | 0 | 0 | 0 | 0 | 0 | 0 | 1 | 3 | 2 |
| Acetone | 3 | 1 | 3 | 1 | 1 | 1 | 1 | 1 | 1 | 3 | 3 | 3 |
| Lead pencil hardness | H | H | H | 2H | 2H | 2H | H | H | 2H | H | 2H | 2H |

*after 8 months storage at room temperature
[1]DMT = 3,5-dimethyl-1,2,4-triazole; DMP = 3,5-dimethylpyrazole Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing secondary mono and polyamines corresponding to formula (I),

by reacting at a temperature of 0° to 100° C. in solution or in the absence of a solvent and at an equivalent ratio of primary amino groups in component A to C═C double bonds in component B of 1:2 to 1.5:1

A) mono or polyamines corresponding to formula (II)

$$X[-NH_2]_m \qquad (II)$$

with

B) compounds corresponding to formula (III)

in the presence of 0.1 to 10 wt. %, based on solids, of a catalyst component C corresponding to formulas (IV) to (XI)

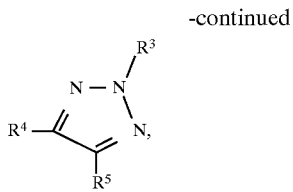

-continued

-continued

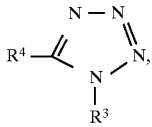 (X)

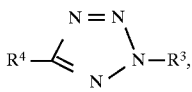 (XI)

and optionally distilling off excess reactants at the end of reaction,
wherein
X represents an m-valent organic residue obtained by removing the primary amino group or groups from a mono or polyamine which has (cyclo)aliphatically bound amino groups and a number average molecular weight of 60 to 6000, and which may optionally contain further functional groups that either are reactive with isocyanate groups or are inert to isocyanate groups at temperatures of up to 100° C., $R^1$ and $R^2$ are the same or different and represent an organic group, $R^3$ represents an $NH_2$ group, a hydrogen atom or an organic group having 1 to 24 carbon atoms, $R^4$, $R^5$ and $R^6$ are the same or different and represent an $NH_2$ group, a hydrogen atom or an organic group having 1 to 24 carbon atoms, or one or more of these groups may optionally be a constituent of another ring system, and m represents an integer $\geq 1$.

2. The process of claim 1 wherein $R^1$ and $R^2$ represent a methyl, ethyl, n-propyl, isopropyl, n-butyl or 2-ethylhexyl group.

3. The process of claim 1 wherein X represents a group obtained by removing the amino groups from an aminoalkylalkoxysilane or an aminoalkylalkylsilane corresponding to the formula

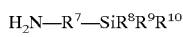

wherein
$R^7$ is an alkylene group with 2 to 6 carbon atoms and
$R^8$, $R^9$ and $R^{10}$ are the same or different and represent chlorine atoms or alkyl and/or alkoxy groups having 1 to 4 carbon atoms.

4. The process of claim 1 wherein X represents a group obtained by removing the amino groups from an aminoalcohol, ethylenediamine, 1,2-diaminopropane, 1,4-diaminobutane, 2,5-diamino-2,5-dimethylhexane, 1,5-diamino-2-methylpentane, 1,6-diaminohexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclo-hexane, 2,4- and/or 2,6-hexahydrotoluylenediamine, isopropyl-2,4- and/or 2,6-diamino-cyclohexane, 2,4'- and/or 4,4'-diaminodicyclohexylmethane, 3,3'-dimethyl-4,4'-diaminocyclohexylmethane, an isomer of diaminodicyclohexylmethanes with a methyl group as ring-substituent, 3- and/or 4-aminomethyl-1-methylcyclohexylamine and/or a polyetherpolyamine having aliphatically bonded primary amino groups.

5. The process of claim 1 wherein $R^3$ represents a hydrogen atom.

6. The process of claim 1 wherein $R^4$, $R^5$ and $R^6$ are the same or different and represent an $NH_2$ group, a hydrogen atom or an organic group having 1 to 6 carbon atoms.

7. The process of claim 1 wherein the equivalent ratio of primary amino groups in component A to C=C double bonds in component B is 1:1.2 to 1.2:1.

8. The process of claim 1 wherein component C is present in an amount of 0.1 to 2 wt. %, based on solids.

9. The process of claim 1 wherein the reaction is carried out at a temperature of 20° to 80° C.

10. A two-component coating composition which comprises, as binder,
a) a polyisocyanate component and
b) an isocyanate-reactive component containing
b1) a secondary mono and polyamines corresponding to formula (I),

 (I)

which is prepared by reacting at a temperature of 0° to 100° C., in solution or in the absence of a solvent and at an equivalent ratio of primary amino groups in component A to C=C double bonds in component B of 1:2 to 1.5:1

A) mono or polyamines corresponding to formula (II)

 (II)

with

B) compounds corresponding to formula (III)

 (III)

in the presence of 0.1 to 10 wt. %, based on solids, of a catalyst component C corresponding to formulas (IV) to (XI)

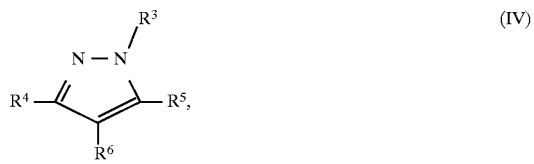 (IV)

 (V)

 (VI)

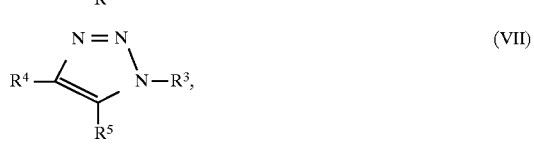 (VII)

 (VIII)

-continued

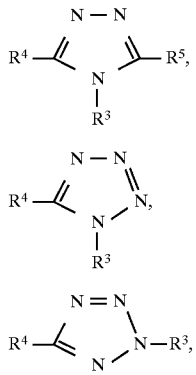

and optionally distilling off excess reactants at the end of reaction,
wherein
X represents an m-valent organic residue obtained by removing the primary amino group or groups from a mono or polyamine which has (cyclo)aliphatically bound amino groups and a number average molecular weight of 60 to 6000, and which may optionally contain further functional groups that either are reactive with isocyanate groups or are inert to isocyanate groups at temperatures of up to 100° C., $R^1$ and $R^2$ are the same or different and represent an organic group $R^3$ represents an $NH_2$ group, a hydrogen atom or an organic group having 1 to 24 carbon atoms, $R^4$, $R^5$ and $R^6$ are the same or different and represent an $NH_2$ group, a hydrogen atom or an organic group having 1 to 24 carbon atoms, or one or more of these groups may optionally be a constituent of another ring system, and m represents an integer $\geq 1$, a compound corresponding to formula (I) and prepared by the process according to the invention, and b2) optionally other isocyanate-reactive compounds, wherein the equivalent ratio of isocyanate groups to isocyanate-reactive groups is 0.8:1 to 20:1, and optionally additives well known in surface coatings technology.

11. The process of claim 10 wherein X represents the group obtained by removing the amino groups from 1-amino-3,3,5-trimethyl-5-aminomethylcyclohexane, 4,4'-diaminodicyclohexylmethane, 3,3'-dimethyl-4,4'-diaminodicyclohexylmethane, hexahydro-2,4- and/or 2,6-diaminotoluene, an isomer of diamino-di-cyclohexylmethane having a methyl group as ring-substituent or 3(4)-aminomethyl-1-methylcyclohexylamine.

12. The composition of claim 10 wherein $R^1$ and $R^2$ represent a methyl, ethyl, n-propyl, isopropyl, n-butyl or 2-ethylhexyl group.

13. The composition of claim 10 wherein m is an integer $\geq 2$.

14. The composition of claim 10 wherein equivalent ratio of isocyanate groups in component a) to isocyanate-reactive groups in component b) is 0.8:1 to 1.2:1.

15. A prepolymer containing urea, urethane, allophanate and/or biuret structures which is based on the reaction product of a polyisocyanate with a mono or polyaspartate prepared in accordance with claim 1, optionally in admixture with one or more other isocyanate-reactive components.

* * * * *